(12) United States Patent
Kalchauer et al.

(10) Patent No.: US 7,550,620 B2
(45) Date of Patent: Jun. 23, 2009

(54) PROCESS FOR PREPARING METHYLCHLOROSILANES

(75) Inventors: Wilfried Kalchauer, Burghausen (DE); Jochen Gross, Tuessling (DE); Wolfgang Zoller, Mehring (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/856,731

(22) Filed: Sep. 18, 2007

(65) Prior Publication Data

US 2008/0071103 A1 Mar. 20, 2008

(30) Foreign Application Priority Data

Sep. 20, 2006 (DE) ........................ 10 2006 044 372

(51) Int. Cl.
*C07F 7/16* (2006.01)
(52) U.S. Cl. ........................ 556/478; 556/466; 556/469; 556/472; 556/476; 556/477
(58) Field of Classification Search ................ 556/466, 556/469, 472, 476, 477, 478
See application file for complete search history.

(56) References Cited

FOREIGN PATENT DOCUMENTS

| EP | 0348902 A | 1/1990 |
|---|---|---|
| EP | 0893448 A | 1/1999 |
| EP | 0893448 A2 | 1/1999 |

OTHER PUBLICATIONS

Catalyzed Direct Reactions of Silicon; K.M. Lewis, D.G. Rethwisch; Elsevier 1993, pp. 1 to 66.
Silicon for the Direct Process to Methylchlorosilanes; Harry Mortem Rong; Dissertation, University of Trondheim, Norway; 1992, p. 53.
Ullmann's Encyclopedia of Industrial Chemistry; Release 2006, 7th Edition.
Handbook of Heterogeneous Catalysis; VCH Verlagsgesellschaft mbH, Weinheim, 1997; vol. 4 "The Direct Process to Methylchlorosilanes", B. Pachaly, pp. 1791-1793.
Harry Morten Rong: "Silicon for the Direct Process to Methylchlorosilanes", 1992, Norges Tekniske Hogskole, Trondheim.

*Primary Examiner*—Elvis O Price
(74) *Attorney, Agent, or Firm*—Brooks Kushman P.C.

(57) ABSTRACT

The invention relates to a process for the direct synthesis of methylchlorosilanes by reaction of chloromethane with a contact composition comprising silicon and copper catalyst, wherein the concentration of oxygen in the chloromethane used is reduced by mixing a) chloromethane which contains oxygen, and b) chloromethane which contains a gaseous boron compound.

15 Claims, No Drawings

PROCESS FOR PREPARING METHYLCHLOROSILANES

BACKGROUND OF THE INVENTION

1. Field of the Invention

The invention relates to a process for the direct synthesis of methylchlorosilanes using chloromethane having a reduced oxygen content.

2. Background Art

Processes for preparing methylchlorosilanes by reaction of silicon with chloromethane in the Müller-Rochow direct synthesis in the presence of suitable catalysts and catalyst combinations are already known. This is described, for example, in CATALYZED DIRECT REACTIONS OF SILICON; K. M. Lewis, D. G. Rethwisch; Elsevier 1993, pages 1 to 66.

In the direct synthesis of methylchlorosilanes, metallic silicon is reacted with chloromethane in the presence of various catalysts, optionally with promoters, with the target product being dimethyldichlorosilane. The mixture of silicon, catalysts and promoters is referred to as contact composition. As over 2,000,000 metric tons per annum of dimethyldichlorosilane are produced worldwide at present, small improvements in the production process such as an increase in the dimethyldichlorosilane selectivity, an increase in the specific space-time yield of dimethyldichlorosilane or an increase in the specific silicon yield therefore have a great economic effect.

The adverse effect of oxygen on the direct synthesis is summarized briefly in a literature review in "Silicon for the Direct Process to Methylchlorosilanes"; thesis, Harry Mortem Rong; University of Trondheim/Norway, Institute for Inorganic Chemistry, 1992 on page 53 in a literature review. Even relatively small amounts of oxygen in the chloromethane permanently reduce the reactivity of the direct synthesis; in addition, the selectivity is also adversely affected by higher amounts of oxygen. On pages 116-117 of that thesis, the adverse effect of oxygen on reactivity and selectivity is described in the context of laboratory experiments. 10 ppm is indicated as a guide value for typical oxygen contents in commercially available, pure chloromethane.

In CATALYZED DIRECT REACTIONS OF SILICON, op. cit., pages 10-11, a value of 99.5-99.8% is given as a typical chloromethane purity for the direct synthesis; this reference does not discuss oxygen as an impurity in any detail. However, those skilled in the art recognize that the removal of oxygen in the ppm range which, for example, can be introduced in traces with the raw materials, is difficult and costly.

EP 893448 A describes the use of boron in the contact composition of the direct synthesis to increase the proportion of dimethyldichlorosilane.

SUMMARY OF THE INVENTION

The invention provides a process for the direct synthesis of methylchlorosilanes by reaction of chloromethane with a contact composition comprising silicon and copper catalyst wherein the concentration of oxygen in the chloromethane used is reduced by mixing together a) chloromethane which contains oxygen, and b) chloromethane which contains a gaseous boron compound. It has surprisingly been found that recirculated chloromethane (b) can be a suitable medium for removing last traces of oxygen from the fresh chloromethane (a). Removal of the traces of oxygen ensures a constant high reactivity and/or selectivity of the methylchlorosilane synthesis.

DETAILED DESCRIPTION OF THE PREFERRED EMBODIMENT(S)

In the inventive process, oxygen from the chloromethane (a) forms relatively high-boiling or solid compounds which no longer have a seriously adverse effect on the direct synthesis. These compounds can, if required, be easily separated from the gas stream.

The process for preparing methylchlorosilanes can be carried out batch wise or continuously; in industrial production, only the continuous variant is employed. Continuous means that the amount of silicon which has reacted and catalysts and optional promoters which have been discharged with the reaction dust are continually replaced, preferably as a premixed contact composition. The continuous direct synthesis is preferably carried out in fluidized-bed reactors in which chloromethane is used simultaneously as fluidizing medium and reactant.

The silicon required is usually ground to a powder and mixed with copper catalyst and promoters to give the contact composition before use in the reaction. Silicon is preferably used in a particle size of not more than 700 µm, more preferably in a particle size of not more than 600 µm, and in particular not more than 500 µm. The silicon usually has a purity of >98%.

A production campaign of the continuous direct synthesis commences with the induction phase. At the beginning of the induction phase, methyl chloride is passed into the heated contact composition. This is followed by the start phase in which crude silane formation begins. The reaction initially proceeds at a low selectivity and reactivity. The stable production phase is then reached. Further contact composition is continually fed in. The production campaign ends when no more chloromethane is passed into the contact composition.

In continuous operation of a reactor, the production rates based on the target product dimethyldichlorosilane decrease in a production campaign after a largely stable production phase. The production campaign therefore has to be stopped after a particular time. A production campaign usually lasts for only a few days to a number of weeks. After a production campaign is ended, the reactor is emptied, recharged with contact composition and brought back to the reaction conditions.

In the direct synthesis, unreacted chloromethane, the gaseous methylchlorosilanes and possibly entrained particles leave the reactor. The entrained particles comprise reacted silicon particles, fine silicon particles, catalysts and promoters/cocatalysts. The entrained particles can, if desired, be separated from the gas stream by means of one or more cyclones, and large entrained particles of contact composition can be recirculated to the reactor. The silane is subsequently separated from residual amounts of dust and unreacted chloromethane and passed to distillation.

The process is preferably carried out in a fluidized-bed reactor, preferably in the temperature range from 250 to 400° C., more preferably from 250 to 360° C., and in particular from 280 to 330° C. Because it requires the smallest capital outlay, the process is usually carried out at or near the pressure of the surrounding atmosphere, i.e. at from about 0.1 MPa to 0.5 MPa, but higher pressures can also be employed.

In a preferred embodiment, the amount of the gas stream is selected so that a fluidized bed of contact composition and gas is formed in the reactor. Unreacted chloromethane and the gaseous methylchlorosilanes leave the reactor. The contact composition is prepared by simple mixing of the individual components at room temperature. Treatment of the contact composition before introduction into the reactor is possible but is not carried out in the preferred embodiment.

In the process of the invention, the form of the copper is preferably selected from among metallic copper, copper alloys, copper oxide and copper chloride. Copper oxide can, for example, be copper in the form of copper oxide mixtures and in the form of copper(II) oxide. Copper chloride can be used in the form of CuCl or in the form of a $CuCl_2$, with corresponding mixtures also being possible. Preference is given to using from 0.3 to 10% by weight, in particular from 0.5 to 7% by weight, of copper in the contact composition, with particular preference being given to from 0.5 to 4.5% by weight.

In the process of the invention, promoters, preferably selected from among zinc, phosphorus, tin and antimony, can be used in the contact composition.

Zinc is preferably used in the form of metallic zinc, also as alloy with copper and, if appropriate, further promoters, zinc oxide or zinc chloride. The amount of zinc used in the contact composition is preferably 0.001-1.0% by weight, in particular 0.010-0.50% by weight.

The tin content of the contact composition is preferably from 5 to 100 ppm, particularly preferably from 10 to 80 ppm, and in particular from 15 to 60 ppm.

The chloromethane (a) is preferably freshly prepared chloromethane, "fresh chloromethane" for short. The oxygen content of the fresh chloromethane is preferably as low as possible but without additional expensive purification steps being employed.

Although the chloromethane synthesis is carried out under inert conditions, industrially produced chloromethane (a) contains from about 10 to 50 ppm by volume of oxygen as a result of the raw materials used, so that no specific oxygen removal is employed.

Those skilled in the art recognize that volatile boron compounds such as lower boranes, for example $B_2H_6$, and organoboranes, for example $Me_3B$, react very vigorously with oxygen. Boron halides, for example $BCl_3$, and boranes also react very vigorously with water. In all cases, relatively high-boiling B—O structures are formed. The properties of boron halides, boranes and organoboranes are described, for example, in ULLMANNS'S ENCYCLOPEDIA OF INDUSTRIAL CHEMISTRY (on CD-ROM); Release 2006, 7th Edition.

In the process of the invention, preference is given to using volatile boron compounds having a boiling point of less than +15° C., more preferably compounds having a boiling point in the range from −40° C. to −15° C., in the chloromethane (b). In particular, $Me_3B$ is used. The concentration of the volatile boron compound in the chloromethane (b) in the process of the invention is at least 50 ppm by volume, preferably at least 100 ppm by volume, and most preferably at least 200 ppm by volume.

In the direct synthesis, the volatile boron compounds can be formed, for example, from the boron or boron compounds present in the raw materials used by means of appropriate reaction conditions and be left at least partly in the chloromethane (b). However, volatile boron compounds can also be added to the chloromethane (b).

After drying with concentrated sulfuric acid as described in ULLMANNS'S ENCYCLOPEDIA OF INDUSTRIAL CHEMISTRY, chloromethane (a) from the reaction of methanol with HCl generally contains from 5 to 60 ppm by volume of $H_2O$, depending on the process parameters selected. The adverse effect of moisture in the chloromethane is summarized briefly in Rong, "Silicon for the Direct Process to Methylchlorosilanes", op. cit., on page 53 in a literature review. It is indicated that water reacts with the methylchlorosilanes to form high-boiling compounds which can lead to undesirable deposits in the reaction system and that water/moisture reacts with the reactive sites on the silicon particles, ultimately leading to a reduction in reactivity.

In a preferred embodiment of the invention, the chloromethane (b) also contains methylchloromonosilanes. Methylchloromonosilanes react with water to form relatively high-boiling Si—O—Si compounds and HCl. The methylchloromonosilanes are preferably compounds of the general formula $H_x(CH_3)_ySiCl_x$, with the proviso that $x+y+z=4$; $z=1$, 2 or 3 and $y=1$, 2 or 3. The chloromethane (b) preferably contains at least 5 mg of methylchloromonosilanes, more preferably at least 10 mg of methylchloromonosilanes, and in particular at least 30 mg of methylchloromonosilanes, calculated as m3, at 0.10 MPa and 20° C.

The methylchlorosilanes formed are separated from the product mixture leaving the reactor after the direct synthesis, for example by condensation. The remaining gas mixture contains unreacted chloromethane and, in addition, varying amounts of inert gases such as nitrogen, saturated hydrocarbons such as methane, ethane, propane and isobutane, unsaturated hydrocarbons such as ethene and propene, and hydrogen. Depending on the method and the conditions for the methylchlorosilane separation, the remaining gas mixture can also contain volatile boron compounds and residues of methylchlorosilanes. This gas mixture can, if desired, in its entirety or in part be purified further in order to increase the concentration of chloromethane and thus obtain a higher reactivity in the direct synthesis. Suitable purification methods are, for example, condensation of the chloromethane and removal of the remaining gaseous constituents, or various forms of distillation or targeted absorption or adsorption.

In a preferred embodiment of the process, the methylchlorosilane separation and any subsequent purification of the gas mixture comprising predominantly chloromethane are carried out in such a way that the volatile boron compounds and any methylchloromonosilanes present therein are not completely removed. The gas mixture is thus preferably used as chloromethane (b).

The mixing ratio of chloromethane (a): chloromethane (b) depends mainly on the reaction rate of the direct synthesis and is generally in the range from 20:80 to 80:20. However, ratios deviating from this can also be established. The mixing of chloromethane (a) with chloromethane (b) is preferably carried out upstream of the direct synthesis reactor and should be as intimate as possible. Temperature and pressure during mixing of the two product streams and also the residence time before they are introduced into the direct synthesis reactor are of subordinate importance.

The reaction products from reaction of the boron compounds with oxygen and possibly methylchloromonosilanes with water are liquid or solid at 0.10 MPa and 20° C. and can, if desired, be separated off in their entirety or in part from the chloromethane mixture before it is fed into the reactor of the direct synthesis. This can be achieved, for example, by filtration, distillation or condensation. However, removal of these compounds is not absolutely necessary in the process of the invention, since the reaction products in the direct synthesis have a much smaller adverse effect than does oxygen or water.

In the following example, unless indicated otherwise, a) all amounts are by mass; b) all pressures are 0.10 MPa (abs.); and c) all temperatures are 20° C.

EXAMPLE

Analysis

The content of low-boiling boron compounds such as trimethylborane in chloromethane can be determined by gas chromatography. The sample is preferably introduced by means of a metering loop. Exclusion of oxygen and/or moisture from the sample containers, sample lines, metering systems and the gas supply has to be ensured during sample handling. Separation is effected by means of a capillary separation column, for example using a 50 m column coated with dimethylpolysiloxane phase, 0.2 mm internal diameter, 0.5 μm film thickness at 35° C. Detection is carried out by means of a specific detector, e.g. a commercial quadrupole mass spectrometer. Detection limits of 10 ppm by volume can be realized in this way, and in favorable cases even lower detection limits are also possible. When the trimethylborane-containing chloromethane sample is doped with oxygen, trimethylboroxin and other boron-oxygen compounds can be detected using the above-described GC-MS system. Molecular oxygen can be detected only when the reactive boron compounds present have reacted completely. The determination of oxygen in chloromethane can also be carried out using this GC-MS system. A detection limit of 2 ppm by volume can be achieved. The oxygen blank of this process has to be monitored precisely.

Procedure (According to the Invention):

In an industrial fluidized-bed reactor system for the preparation of methylchlorosilanes, as described in the HANDBOOK OF HETEROGENEOUS CATALYSIS: Edited by G. Ertl, H. Knörzinger, J. Weitkamp, VCH Verlagsgesellschaft, mbH, Weinheim, 1997; Volume 4 "The Direct Process to Methylchlorosilanes (Müller-Rochow Synthesis)", B. Pachaly, pages 1791-1793 and FIG. 1, the methylchlorosilane separation and recycle gas purification were operated so that 300 ppm by volume of trimethylborane and 49 mg of chloromonosilanes calculated as m3 at 0.10 MPa and 20° C. remained in the recirculated chloromethane. The methylchlorosilanes were a mixture of dimethylchlorosilane, methyldichlorosilane, methyltrichlorosilane, dimethyldichlorosilane and trimethylchlorosilane.

The fresh chloromethane used contained 30 ppm by volume of oxygen and 20 ppm by volume of water. Recirculated chloromethane and fresh chloromethane were intimately mixed in a ratio of 60:40, passed through a gas filter and introduced into the fluidized-bed reactor. A light-colored solid having the following composition: 44.0% by weight of silicon; 7.4% by weight of chlorine; 17.4% by weight of carbon; 25.3% by weight of oxygen; 5.1% by weight of hydrogen; 0.2% by weight of boron; deposited in the gas filter. The oxygen content and water content of the gas mixture downstream of the gas filter were below the detection limit. This confirms that oxygen and moisture, when present, are removed from the fresh chloromethane by means of boron compounds and optional methylchlorosilanes in the recirculated chloromethane.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for the direct synthesis of methylchlorosilanes by reaction of chloromethane in a reactor with a contact composition comprising silicon and copper catalyst,
   wherein the concentration of oxygen in the chloromethane is reduced by mixing
   a) chloromethane which contains oxygen, with
   b) chloromethane which contains a gaseous boron compound,
   wherein said mixing takes place prior to addition of a) and b) into the reactor.

2. The process of claim 1, which is carried out continuously.

3. The process of claim 1, wherein the volatile boron compounds present in a product mixture leaving the reactor after the direct synthesis are not removed completely and the resulting gas mixture comprising predominantly chloromethane is used as chloromethane (b).

4. The process of claim 1, wherein the mixing ratio of chloromethane (a): chloromethane (b) is from 20:80 to 80:20.

5. The process of claim 3, wherein the mixing ratio of chloromethane (a): chloromethane (b) is from 20:80 to 80:20.

6. The process of claim 1, wherein the concentration of volatile boron compounds in the chloromethane (b) is at least 50 ppm by volume.

7. The process of claim 3, wherein the concentration of volatile boron compounds in the chloromethane (b) is at least 50 ppm by volume.

8. The process of claim 4, wherein the concentration of volatile boron compounds in the chloromethane (b) is at least 50 ppm by volume.

9. The process of claims 1, wherein the chloromethane (b) additionally contains methylchloromonosilanes.

10. The process of claims 3, wherein the chloromethane (b) additionally contains methylchloromonosilanes.

11. The process of claims 4, wherein the chloromethane (b) additionally contains methylchloromonosilanes.

12. The process of claims 6, wherein the chloromethane (b) additionally contains methylchloromonosilanes.

13. The process of claim 9, wherein the chloromethane (b) contains at least 5 mg of methylchloromonosilanes per m³ at 0.10 MPa and 20° C.

14. The process of claim 9, wherein the methylchloromonosilanes present in the product mixture leaving the reactor after the direct synthesis are not removed completely.

15. The process of claim 13, wherein the methylchloromonosilanes present in the product mixture leaving the reactor after the direct synthesis are not removed completely.

* * * * *